(12) United States Patent
Helpert

(10) Patent No.: US 11,810,574 B1
(45) Date of Patent: Nov. 7, 2023

(54) VOICE-DRIVEN INTERNAL PHYSIOLOGICAL IMAGING

(71) Applicant: Leslie Helpert, New York, NY (US)

(72) Inventor: Leslie Helpert, New York, NY (US)

( * ) Notice: Subject to any disclaimer, the term of this patent is extended or adjusted under 35 U.S.C. 154(b) by 0 days.

(21) Appl. No.: 18/309,830

(22) Filed: Apr. 30, 2023

Related U.S. Application Data

(63) Continuation of application No. 18/055,831, filed on Nov. 15, 2022.

(51) Int. Cl.
*G10L 17/04* (2013.01)
*A61B 5/00* (2006.01)
*G10L 25/66* (2013.01)
*G10L 17/02* (2013.01)
*A61B 5/055* (2006.01)

(52) U.S. Cl.
CPC ............ *G10L 17/04* (2013.01); *A61B 5/0073* (2013.01); *A61B 5/055* (2013.01); *G10L 17/02* (2013.01); *G10L 25/66* (2013.01)

(58) Field of Classification Search
None
See application file for complete search history.

(56) References Cited

U.S. PATENT DOCUMENTS

| | | | |
|---|---|---|---|
| 2020/0077892 A1* | 3/2020 | Tran | A61B 5/1117 |
| 2020/0193271 A1* | 6/2020 | Allen | G06N 20/00 |
| 2023/0004801 A1* | 1/2023 | Farabet | G06V 10/82 |
| 2023/0015714 A1* | 1/2023 | Shvartzman | A61B 5/02055 |
| 2023/0078832 A1* | 3/2023 | Wiegman | G06N 20/00 |
| | | | 703/8 |
| 2023/0152801 A1* | 5/2023 | Park | G05D 1/0246 |
| | | | 706/20 |

* cited by examiner

*Primary Examiner* — Jakieda R Jackson
(74) *Attorney, Agent, or Firm* — Kathryn Perales

(57) ABSTRACT

A system and method of capturing a voicer's voice data to illuminate features of their own physiology and produce voice-driven internal imaging. Data encoded within the voice is captured, decoded, modeled and simulated. Using vibrations of a voicer's voice as the input, features of their own physiology are outputted in the format of an internal image.

15 Claims, 4 Drawing Sheets

VOICE-DRIVEN INTERNAL PHYSIOLOGICAL IMAGING

BACKGROUND OF THE INVENTION

The background of the invention relates to two histories; the history of internal imaging and of the human voice as a utility in the context of computer science.

Natural Language Processing (NLP) has propelled communication technology forward. Combining linguistics, computer engineering and areas of neuroscience, NLP makes use of syntax and semantics, the Rules and structures implicit within generative grammar: patterns supporting network development. Remarkably, these expression-relevant patterns are present not only in the constructs of linguistics, but are also deeply nested within auditory-neurological functions, and NLP has helped bring this to light, bridging biological networks and intelligent machines.

NLP is a "cutting edge of technology," but its enterprise relies on one of the oldest "communication technologies," language, whose origins are approximately 150,000 years old. However, there is an even more ancient communicative-biological partnership than paired linguistic and auditory-neurological patterns, outside the direct scope of NLP's focus. The non-lingual voice, a "raw-voice" stripped of language-relevant facets and outwardly-engaging intentions, is a composite of signals, packed with waves in transfer, vibrations and harmonic structures. Its function of internally propagating within a physiology out-ages the advent of language by 2.8 million years—in fact, it is language's harbinger.

Evolving "sentience"—or, what is often referred to as "the body's language," that is, the capacity for perception and feeling, is a developmental objective in the field of Artificial Intelligence (AI), an objective which NLP's contributions have greatly supported. While NLP has empowered machines to comprehend many facets related to language and communicative expression, by origin, its window into biological sentience advances from a cognitive-centric vantage point. Sentience, however, belongs to the whole body. NLP has not thoroughly prioritized exploring the impact one's non-lingual, vibrationally-rich voice has on their own, interconnected physiological systems from a whole-body perspective. Thus, in regards to the aim of building both safe and sophisticated bridges between biological and artificial life, NLP has overlooked a centerpiece utility and deeply-seeded resource for opening wide doors, not only within communication technology, but in fields reliant on pattern recognition and network design.

Since its first noted use 125 years ago, internal imaging technology has been dependent on signals of mechanical or electromagnetic wave generation. (I.e., ultrasound imaging uses high-frequency acoustic waves, magnetic resonance imaging uses radio waves, and X-ray imaging uses X-rays, which are electromagnetic waves with wavelengths between ultraviolet and gamma waves.) "Wave-based" internal imaging technologies, by design, necessitate provoking a biological system with waves that are not "endogenous" (meaning, not internally occurring) to the body, but introduced exogenously.

Exogenous, or "externally caused," is synonymous with the term "intrusive," which is interchangeable with "invasive." While certain medical imaging is notably less "invasive" than others, to this day, all internal imaging is interruptive to a body's natural oscillation, as externally triggered waves introduce foreign stimulation in order to relay details of internal structure. Internal imaging technology has not made use of the resource of the endogenous voice-a naturally occurring wave-based formula inherently familiar to the body system. It has overlooked a non-intrusive, endemic resource for producing in-vivo, real-time physiological imaging that requires neither expensive apparatus, exogenously introduced wave stimulation, nor access to medical imaging facilities.

SUMMARY OF THE INVENTION

A voice-image system and method are described firstly through select, substantial frameworks integral to the system and method's foundation. Please note that as a convention, terms which begin with bold capital letters may be found in the glossary of this specification.

One framework is evaluating the invention as an overarching inverse mathematical problem, umbrellaing solved, smaller, "micro-stage" Inverse problems essential to its physical solution. In this instance, an Inverse problem is described as the condition for solving a case where an output is known, but the input or the system characteristics (i.e. Parameters, features, functions, etc.) are unknown. The solution of the overarching Inverse problem is, in fact, the ultimate model of the invention—that is, from the information of a user's voice, an image of the Voicer's internal physiology is produced. This ultimate model is considered the "macro-state," a solution to an Inverse problem that is supported by solutions of "micro-stage" Inverse problems inherent to the invention process; as understory layers within a forest provide stability for the whole forest ecosystem.

In solving for the unknown dynamic components between the voice and the physiology, the voice and the physiology each have explicit opportunities to serve the role of being either the "known" or "unknown" observation within an inverse equation. In first stages, a voice is positioned as the "known observation"; an output of collective signals made, dominantly, of acoustic, mechanical waves. The objective is to learn (and Meta-learn) information encoded within a voice (specifically, the vocally-propelled, inwardly impacting, vibrational system-response pathways that confirm attributes of a physiological state). From this base, having learned the "meaning" of a voice relevant to the objective, a voice is reconstructed from its causal parts.

In other stages, the physiology is regarded as the "known output," for example, in machine-learning processes where data from Non-imaging signal-capturing instruments is Cross-referenced with internal imaging technologies. The physiology is positioned as a "known output," as well, when computationally rendered Configured geometries of a physiology are reconstructed utilizing the voice as the reconstructive agent. Ultimately, the relationships between a Voice-signal and its corresponding physiological expressions are the set of characteristics discovered in the voice-system training model which allow for the production of a Voice-driven internal physiological image. (To note, "Voice-signal," rather than "sound-signal," is used in the context of the invention, referring to inwardly-impacting Fundamental wave properties and Wave behaviors instigated by Voice-signals and occurring within a Voicer's own physiology, rather than "what is heard," which relates to audible, externalized sound.)

Micro-stage Inverse problems support model development, and include inverse methods that are both specific and consistent operations, interwoven throughout the whole system. "Micro-stage" problems, for example, include processing Voice-signals, Parameterizing data, filtering and decrypting system "noise." Handling differential equations, determining Nodes (states) and "edges" (relationships) within graphs, reduced order operations, and, most generally, all processes of synthesizing biometric data are largely based on solving Inverse problems.

Voice Kernels

A crucial system-wide "micro-stage" Inverse problem is the means for discovering the fundamental Nodes of the Voice-physiology, called Voice kernels.

It is from a scrutinizing statistical and mathematical approach that a Voice-physiology (and a digitally-learned Voice-network) can be learned as emerging from a system of Voice-signal Rules that generate combinations of executions, operations or transformations, in relation to a physiology; a causal network of signal responses. These are named Voice kernels. (In this disclosure, "kernel" is etymologically more relevant to the denotative biological roots of the term, meaning "heart," "nugget," or "central essence," rather than the use of "kernel" associated with various pre-existing computer science applications.)

Voice kernels are insightful points learned within the Voice-physiology. Logically, they are mathematical Rules, axiomatic, mathematical parts (or relationships) relevant to describing a Voice-network in terms of reduced operations, formulaic orientations and transformations. A Voice-network can justify behaviors of the asset through learned Voice kernels, their Rules and "rewrite steps" (emergent patterns and timelines), likening an evolution of a Voice-physiology behavior to a rewriting system. This way, in combination with effective algorithmic applications, the Voice-physiology can be described in terms that are metrically translatable, functional, and efficaciously graphable.

To clarify: the use of "Voice-physiology" refers to the biological asset and the biological model of the voice within the physiological system, whereas the Voice-network refers to the process of digitally learning and operating a synthesis/model of a Voice-physiology domain. In certain cases, the use of terms overlaps.

Learning Voice kernels entails solving Inverse problems, processes of finding (or reducing) the underlying Rules of a system from its geometrized features: objects, patterns, topologies, motifs, ranges, scales and dimensions. Particularly, as extrinsic and intrinsic factors are apt to change the regulatory functions of the domain, Voice kernels help to identify what is universal within a Voice-physiology. For instance, a Voice kernel can possess the foundational "set of directions," so to speak, of an emergent geometrized propagational path, wherein one segment of the Rule maintains stable oscillation, but another segment is "updated" (or replaced) with changing values of periodicity. The replaceable portion of the Rule's parts (in this example, the periodicity, or wavelength) can justify patterns of transformation or an expression of kinetic energy within a state. In another example, a Rule can be the formulated, foundational terms that evolve as the Normal modes of a biological system, wherein sinusoidal wave components oscillate in scalable, coupled and fixed phases. Cartographically delineating Voice kernels within a Voice-network is synonymous to the Inverse problem method of determining causal factors (inputs) that influence observable behaviors (outcomes). For example, elements of a Voice kernel are factored by gauging variations in Frequency response along a Transfer path of a Voice-physiology, effectually gleaning Rules of system movement.

To note, Voice kernels can be evaluated as individual, discrete structures, or collectively, for example, within clusters or Neighborhoods. Like stars in the sky, they aid in navigating space, giving light to the "vibrational environment" within a Voice-network, revealing edges and Nodes, supportive, ultimately, to the process of translating structural details, formulating and facilitating Voice-driven internal imaging.

Charting the Uncharted

Approaching the invention as a series of inverse processes is well-fostered by two additional frameworks, each well-positioned to support "solving for the unknown," to search out features and designs, to chart uncharted territory; to exploratively learn and Meta-learn a system. One framework considers the Voice-physiology as a Dynamic system of signal-and-response relationships.

A Dynamic system describes a non-static system whose states are dependent on change and the impact of change. Dynamic system models are, in essence, supportive of multidisciplinary operations (from modeling molecules to climate change). Particularly, they are useful for fields of computational biology, as biological systems, such as a Voice-physiology, are filled with micro-level influential factors, deep dimensions, are often chaotic, "noisy," and difficult to predict; they're dynamic. A Dynamic system model highlights the value of complexity (non-linear, stochastic processes) within a system's whole and its parts. Approaching a Voice-physiology as a Dynamic system offers engineering insights into interconnected or coevolving foundational Rules and emergent features, and a means to frame uncertainties as Optimization problems. In this way, a Dynamic Voice-physiology system is set up as a rich domain; rich in uncertainty, rife for queries, for probabilistic applications and rigorous Optimization methods. By implementing this perspective, a Voice-physiology can be regarded as a system of generative change, where, for example, successive states emerge from current states through distinct principles or functorial Rules, supporting an axiomatic approach for learning a Voice-network (re: Voice-kernels). Through a Dynamic system framework, the process of procuring an internal image from Voice-physiology data can be regarded as harvesting a Dynamic system.

Another indispensable, central invention framework is the system-wide application of Evolutionary computation (EC), a family of methods inspired, in essence, by facets of biology (such as adaption and natural selection). An example of an EC operation within the domain of the Voice-physiology could be a search within a data structure wherein the data includes a range of voice-produced frequencies that are interacting with various physiological features. Here, EC may search the Voice-network in a "biologically-inspired" capacity, recombining, mutating and evolving candidate solutions relevant to a Fitness function, determined, in this case, by what combined features of the voice are of most significance to the impacted physiology.

EC methods are useful not only when potential solutions are uncertain, but also when what is being searched for is not yet certain nor clearly defined, which makes it prime for evolving a Voice-network model that is fundamentally filled with unknown characteristics. EC methods align with the often stochastic, non-linear nature of the Dynamic system of the Voice-physiology, one reason being evolutionary algorithms, as they are biologically inspired, rely on stochastic and non-linear methods of operation. This makes EC well-suited for learning systems with random (or random-seeming) variables, as is the system of a Voice-physiology. EC is useful throughout the entire engineering process: in feature selections, Parameterizations, Optimizations, learning topologies, and Meta-learning data provided by other contributing ML methods. For example, Generative learning approaches for data-augmentation are Meta-learned and evolved through EC, supporting Optimizing network architecture.

Though the invention also employs strategies outside of EC, Dynamic systems modeling and inverse methodologies, these three described frameworks notably provide descriptive context for the biomimetic approach of the invention. The aforementioned frameworks support the operative aim to learn and Optimize a Voice-network, to configure well-represented data structure and essential bases to advance the model for the use of producing internal imaging.

Methodology of Steps

For optimum analysis, a Voice-physiology is best understood as a vibrationally-rich whole body, its area and sub-areas, through a Shape-based approach of intrinsic symmetries, ratios and geometries. A Voice-physiology is measured through two classifications of instrument types. One classification is Non-imaging signal-capturing instruments, examples being accelerometers and pressure sensors. The other classification of measuring instruments is internal imaging technologies (for example, ultrasound). Cross-referencing between internal imaging and Non-imaging signal-capturing instruments supports the aim of decoding physiological features from a Voice-signal, central to producing Voice-driven internal physiological imaging.

In various method stages, machine learning (ML) processes ascertain Voice-physiology measurements. Essential measurements include an analysis of Fundamental wave properties (Voice-signal properties) such as frequency, wavelength and periodicity, as well as more complex propagational behaviors (Wave behaviors) and variables relevant to voicing within the heterogenous physiological terrain.

Learning a Voice-physiology requires a Pipeline of Computational engineering components (CECs). An initial CEC is a Phenomenological (first) Digital twin, a digital representation of a Voice-physiology. It obtains data in (mostly) live experiments, partnered to its "biological twin" (a Voice-physiology), and is learned through foundational ML methods. The twin is queried by a model of strategy, an Optimizer, which utilizes methods including (but not limited to) Evolutionary approaches (EC). Optimization supports the development of a Second-generation digital twin, a hybrid, "semi-empirical" model. The Second-generation twin is "packed" with mechanistic modeling features, mathematical and Physics-based formulaic insights about the domain. It is "hybrid," however, as it is also "semi-empirical," informed (and Optimized) by statistical data gained in (predominantly) live training settings, operating along with a biological twin. In advanced stages of Second-generation digital twin Optimization processes, Configured geometries of physiology become calculable from a Voice-signal. Final Pipeline stages include a Simulator that outputs a Voice-signal from an input of Configured geometries of physiology, that is Optimized until a Voice-signal output and a Configured geometry of a physiology are a precise match. A final-most stage of the CEC pipeline is, simply, the converse act; wherein an input of a Voice-signal is outputted as an internal physiological image.

The nature of the CEC Pipeline can be visualized in full as a mountain-shaped, inverse-order process: the first half of the "inverse" sojourn is an upward slope, or ascent, involving digitally extracting features of physiology from the voice (voice data). Its solution is expressed when arriving to the mountain's peak, or apex, wherein a Configured physiology has been derived from voice data. The "mountain journey," however, is not complete, until finishing a careful "descent," during which the voice is now, conversely, extracted from a Configured physiology. The accomplishment of "reaching the other side" of the mountain is confirmed by an "endpoint" success; that is, the voice has been leveraged as an internal physiological imaging system.

DETAILED DESCRIPTION OF THE INVENTION

Figure 1:
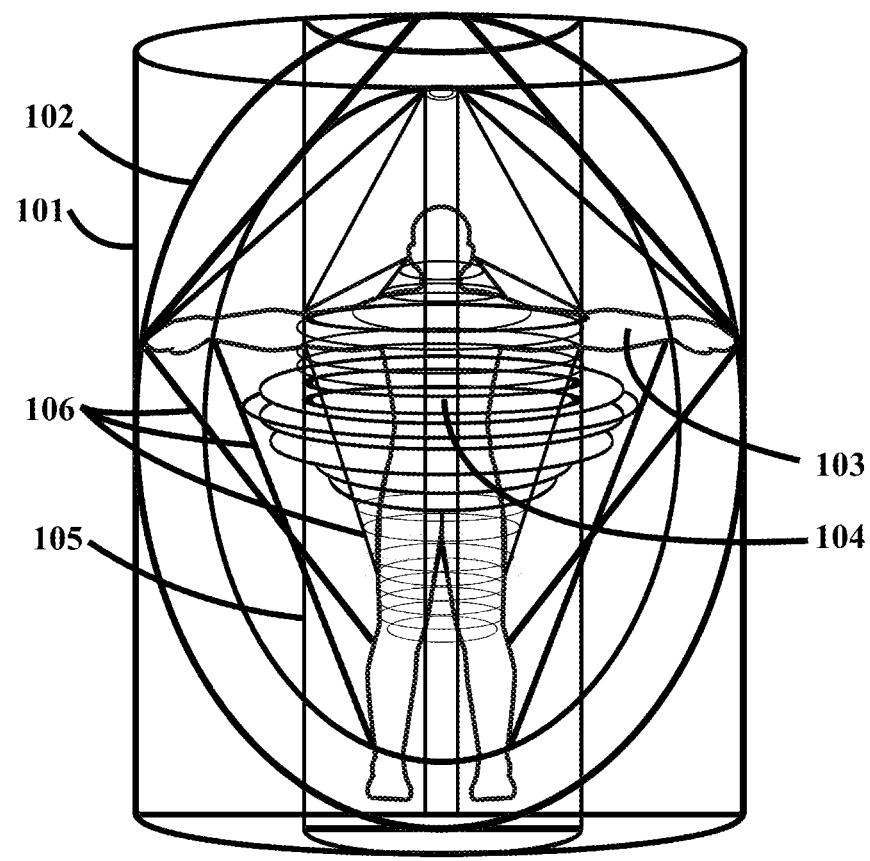
FIG. 1 illustrates a Voice-physiology, an entire physical body and area it encompasses, considered as a whole region and subregions, Spheres and Slices, based on the resonance of symmetries, ratios and geometries.

Referring to FIG. 1, to obtain useful data for Voice-driven internal imaging, a Voice-physiology 101 is demarcated to be within the perimeter of geometries relevant to the area of the body. A Voice-physiology's area includes the space 101 around the body as well as the body's physical form 103 and its physiological attributes. A region of the Voice-physiology called a "vocal body area" 102 extends to an arm's length distance of space around the physical form 103, outlining a proliferative ovoid shape 102 that nests the physical body structure 103. Assessing the Voice-physiology through a geometrical lens is important for considering its underlying, conductive forces and features. The "vocal body area" is accessed by the limbs (and rotationally-oriented structures of the body, such as the hips and shoulders). It can be regarded as an area for commandeering the voice, for inwardly ushering the voice with command to create the strongest vibrational resonance (and, therefore, the heartiest execution and sustain). Additionally, "the vocal body area" 102 is the most direct region from where a fundamental basis for voicing, the breath, is drawn. Symbolically, the vocal body area can be likened to the resource of an egg "white," vitalizing the development of a "yolk" (or—in this case, the physical body 103).

While significant insight about the Voice-physiology is gained by evaluating its complete region, it is also considered in sectionalized aspects of Spheres 101, 105 and Slices 106. Spheres and Slices are terms most often interchangeable. However, to specify, "Spheres" dominantly describe an area of cylindricality or triangularity within a Voice-physiology, while "Slices" can describe lines, connected points, or various intersectional "cuts" within Spheres. In all cases, a Voice-physiology is based on its architectural ratios and symmetries. Spheres and Slices can encapsulate highly resonant areas of the physiology, vibrationally correlating structures or distinct spatial distances. For example, 104 points to a highly resonant area located at the center of the diaphragm, positioned within an inner-most Sphere of the body and at the center of geometries related to the symmetry of a Voice-physiology. Voice-physiology Spheres and Slices support the first stage of the invention, which is to obtain useful metrics of the voice, in the form of data. To clarify, however, regionalized Spheres or Slices of a Voice-physiology (even when referred to as "domains") are not inextricably bound to the classified domains or subdomains of a digitally-learned Voice-network 501, and vice-versa. Representing a Voice-physiology and Voice-network 501 both rely on well-Parameterized regionalizing, with the ultimate, shared incentive to both locally and globally exploit underlying functions and geometrized features of a system. In regards to obtaining measurements, both a whole Voice-physiology and its subregional Spheres and Slices support the determination of where Signal-based measuring instruments may be best directed.

Instrumentation

Figure 3:
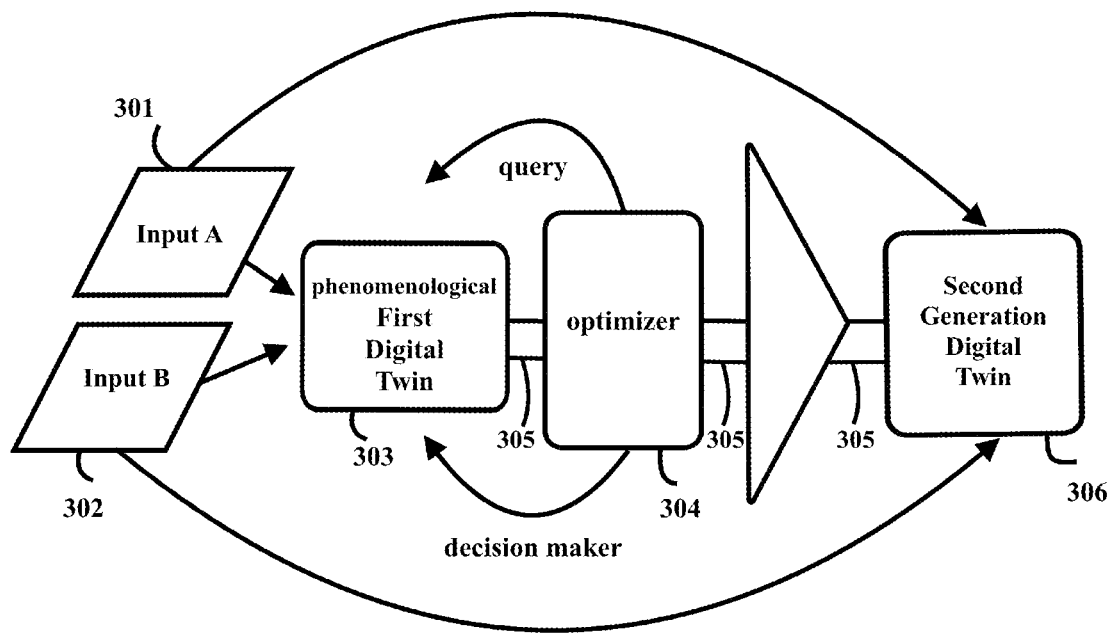
FIG. 3 is a flowchart and diagram showing the advancement of a CEC Pipeline, including a first Phenomenological Digital twin and the development of its data.
Figure 4:
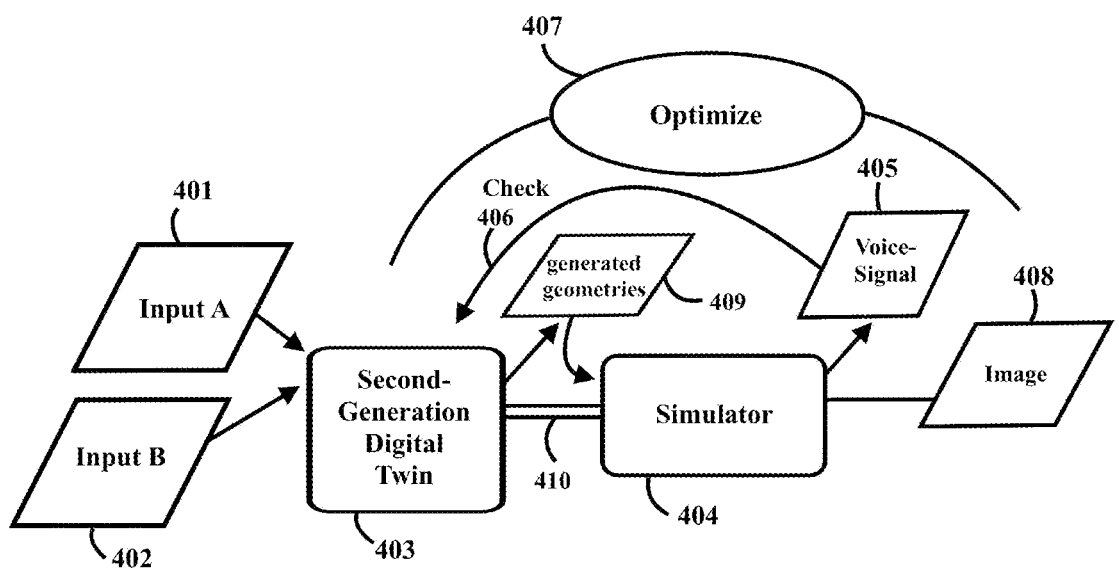
FIG. 4 is a flowchart and diagram showing the advancement of the CEC Pipeline, including developing a Second-generation digital twin.

The voice, as described, is not measured in realms of lingualized communication or by functions related to a physically-externalized sonic output, but, rather, learned by its vibrational influence within a physiological domain. Signal-based measuring instruments capture essential data about Fundamental wave properties and Wave behaviors (meaning, the characteristics of voice-relevant vibrational propagation within a Voice-physiology). Referring to FIGS. 3 and 4, Signal-based measuring instruments used to gather raw voice data (ultimately, "input") are separated into two main classifications 301, 401, 302, 402.

One classification of instruments includes Non-imaging signal-capturing instruments 301, 401, positioned to collect useful signal-based data about a Voice-physiology, for example, assessing points along a Voice-signal Transfer path. Non-imaging signal-capturing instruments are, by design, technologies producing an output of signal-based data that is not a visual image of an internal form (whereas the term "visual image" denotes a technology such as a picture-based X-ray or MRI). Examples include accelerometers, pressure sensors, acoustic and/or elastic wave sensors (for example, Geophones or acoustic Interferometers), and piezoelectric probes.

Figure 2:
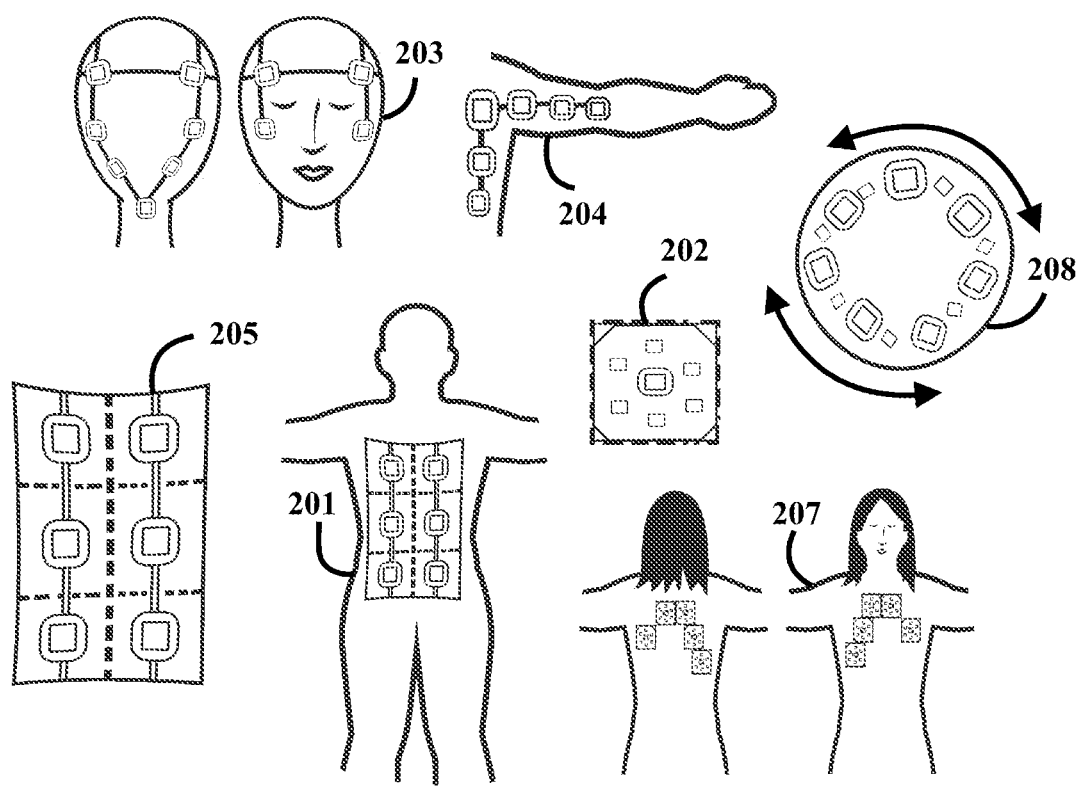
FIG. 2 is a schematic representation of multiple versions of a modular Rig, which is a malleable unit comprised of accelerometers and signal-capturing instruments, adjustable to set specifications of a Voice-physiology and ambition of experiment.

Non-imaging signal-capturing instruments can be outfitted onto a unit—dubbed a "Rig," several embodiments of which are shown in FIG. 2—a transformable, malleable, multi-modal instrumented array, capable of modularly functioning as a suit, vest or patch 202. A Rig is primarily outfitted with accelerometers placed between 2-to-4 inches apart, positionally adjustable in various arrangements, for instance, in circular or square "patchwork" formations 205, wherein each piece is manufactured to agilely connect to its neighbor piece. The adjustive adaptiveness of a Rig caters to different surfaces of a body and, as well, supports obtaining the clearest system-wide (global) and specific (local) information about both the intrinsic and emitted vibrations of the human body. In one embodiment, a Rig may be arranged as a group of six accelerometers on the back body 201, where each accelerometer is positioned on the left and right side of the spine's divide. In this case, accelerometers may be precisely adjusted two inches apart, constructively placed in approximation to specific spindles of the skeletal muscle, which are areas particularly responsive to vibration and resonance.

A Rig may be applied to any surface of a body, for example, the side-body and arm 204, or along the face, neck and head 203. Two or more Rigs may be placed on opposite surfaces of a body or body part at one time, such as the front and back regions of the skull and face 203, or applied to symmetrical points on opposite hands and feet. 207 points to a pairing instance where one Rig is placed on the anterior chest region in conjunct with a dorsal Rig, located over the thoracic region. Two or more Rigs may be positioned along the surfaces of adjacent or non-adjacent body parts, for example, the lateral lumbar region and thigh. A Rig, placed on a lower diaphragmatic area of the body may be paired with a Rig assembled at points along the collar bone.

A Rig is designed, specifically, to accommodate "Bilateria." "Bilateria" refers to a Shape-based scientific grouping of animal type, under which humans fall; symmetrically composed of front, back, top and bottom components. Correspondingly, this composition is conducive to resonant-rich internal architectures-thus, the Bilateria design naturally supports conducting voice. A Rig is structured, in this sense, to consider the "vibrational, architectural geometry" of the Voice-physiology.

As well as being positionally orientable to select anatomical regions, a Rig can also be finely rotated in degrees (clockwise or counter-clockwise) 208, to measure intervals, for instance, like transmission and arrival times of a Voice-signal source and receiver. In this way, a Rig is designed for a thorough investigation of the vibrational Voice-physiology, providing both discrete information and, as well, means for deducing more continuous values about the domain.

In addition to accelerometers, a Rig may incorporate other Non-imaging signal-capturing instruments, such as pressure sensors, acoustic or elastic wave sensors (for example, Geophones or acoustic Interferometers,) or piezoelectric probes. In some cases, such as in instances of Cross-reference learning (see Cross-training section), a Rig can accommodate an addition of internal imaging instruments, such as an ultrasound device. The accelerometers (and any Non-imaging signal-capturing instrument components of the Rig) are secured in protective housing and positioned to offer the greatest subsurface information about the area being measured.

A Rig's accelerometers are most often calibrated for assessing vibrations between ~3-1000 Hz. The spectrum of ~3-1000 Hz accommodates naturally-occurring biological vibrations (most dominantly between 3-30 Hz) as well as the range of human voice vibration (generally between 150-300 Hz). Additionally, ~3-1000 Hz covers frequency ranges of (at least) second and third harmonics, or "overtones," within the upper structure of the voice, as the frequencies of upper harmonics are the successive integer multiples of a fundamental, base frequency. (I.e., by principle, a 200 Hz fundamental frequency should have a second harmonic of 400 Hz and a 600 Hz third harmonic, all which fit within the calibrated ~3-1000 Hz range of a Rig's accelerometer.)

In contrast to the emission of naturally-occurring vibrations of biological features (internal organs, body fluids, etc.) and vocal ranges between ~3-300 Hz, human hearing (audible "sound") extends from 20-20,000 Hz. However (to reinforce the approach of learning a Voice-physiology, as stated in above sections), a voice is not gauged for its relationship to audial, lingual or psychologically-associated qualities, nor by its externally-directed effect on others, but rather by its internally-impacting vibrational capacity within a physiology.

"Cross-Training"

Referring again to FIGS. 3 and 4, another classification of instruments used to obtain Voice-physiology data (input) is internal imaging technologies 302, 402. These technologies can include, but are not limited to, ultrasound techniques (such as Doppler and endoscopic ultrasound), magnetic resonance imaging (MRI), acoustic tomography, 3-D echocardiogram and magnetoencephalography (MEG). An incentive for engaging internal imaging in the process of collecting Voice-physiology data is to "Cross-train" (Cross-reference) measurements of data from Non-imaging signal-capturing instruments with internal imaging-based data, obtained in either concurrent or successive instances.

A Cross-referential ML strategy makes use of data obtained, specifically, through this twofold approach of measuring a Voice-physiology. For example, Voice-physiology data acquired through a Rig is referentially correlated with data acquired through ultrasound. In this case, Rig-based data is learned and Meta-learned in relation to ultrasound-based data, supporting the advancement of a Voice-signal to describe a physiological state. Through ML, the role of relaying "visual" information about the domain is transferred from internal imaging technologies to a voice and its signals. This approach (in addition to other central signal-processing methods) supports mapping voice-attributes to Physiological geometries, and helps to progress the stages of developing the model of a Voice-network 501.

In addition to Cross-referencing data obtained by Non-imaging signal-capturing instruments with the data obtained by internal imaging technologies, Cross-training can also include instances of Cross-referencing data obtained by Signal-based measuring instruments within the same classification. For example, Cross-referential learning strategies can be applied to data obtained by two Non-imaging signal-capturing instruments, such as an accelerometer and pressure sensor, or between two internal imaging technologies, such as an MRI and ultrasound.

Areas of Measurement

The Voice-physiology is learned through a relational lens, with the aim of deeply gaining insight about the Voice-signal (vibrational) impact within the whole physiology. In acquiring data about the domain, all central physiological parts are considered useful, including musculoskeletal, endocrinal, lymphatic, respiratory, digestive and nervous systems; body fluids, hard and soft tissues and intra-system activities. A voice propagates through heterogenous mediums at different speeds, therefore, building a robust Voice-network 501 model relies on obtaining intricate system-wide domain insights.

Distinguished Voice kernel-rich areas of the domain provide significantly substantial and concentrated data. For example, a navel ("umbilicus") is valuable for its thin-skinned features, supportive of acquiring subsurface information. Additionally, it is the symmetrical "center" of the area of the body, which aligns with a system-wide, Shape-based approach for learning. Possessing thousands of nerve endings, the navel directly connects multiple organs; the abdomen, spinal cord, bladder and urethra. Collecting data from a navel area can entail obtaining signals concurrently through a Rig and internal imaging.

Other measured areas of a Voice-physiology can include the axis-atlas of the occipital region of the spine, or the interstitial network of the extracellular matrix (a signaling path communicating non-linearly through non-adjacent parts of the entire body). Key areas for obtaining Voice-physiology measurements also include "resonant chambers" such as the interior cavity of a face (and sinus region), or the smooth muscle composition of hollow organs, which performs a wide range of regulatory signal-based functions.

Measuring "isolated" limbs means gauging voice-instigated response patterns in areas such as an arm, or in body parts that are nonadjacent to traditionally considered "voice-relevant anatomy" (trachea, pharynx, larynx, glottis, etc.). Additionally, measuring isolated limbs supports learning a Voice-physiology from areas less directly impacted by respiration-influenced structural shifts in hard and soft tissues (but wherein blood pressure or other fluid fluctuations are assessable).

Through Signal-based measuring instruments, a Voice-physiology is ultimately searched for its Systemic voice energy, and, effectively, how that energy interacts with other energy systems in the body. Therefore, a learning approach of the Voice-physiology includes assessing the signal inter-activity of the domain in relation to the voice, including the electromagnetic and piezoelectric behavior of cells, heart valves, neurons, epidermis and bones.

While mechanical and electromagnetic waves possess significant differences, the impact of their activity within a shared domain is inevitably intersectional. For example, when a voice wave penetrates the internal physiology, waves can attenuate (or lose energy) within a medium. A medium (for instance, organ tissue) can reflect, refract or absorb the voice "energy" as expressed heat generation. To consider a Dynamic Voice-physiology system, all contributing factors influencing the domain, such as mechanobiological waves, pressure levels, and thermodynamic processes, are taken into account. It's important to obtain contextual whole-system information from the domain, particularly through the lens of considering its material, Dynamic state as a product of formulaic, multivariate wave interactions and responses.

From the earliest stages of instrumented measurements, a Voice-physiology is approached and searched as an actively changing Dynamic system. Sectionalizing assemblies of Spheres and Slices supports the hearty acquisition of Voice-physiology data, an inevitable complexity of statistics prevalent within a Dynamic system, which ML approaches make use of: uncertainties, system noise, interference patterns, passive and active forces.

Features: What Is Measured

Charting voice in the body necessitates gaining insight about the Voice-physiology Transfer path, that is, the internal interplay of dynamical activity between a Voice-signal and the vibrational structures along its course. "Vibrational structures" comprise the entire physiology (as there is no object known that does not have a vibrational disposition). In this case, analyzing a Transfer path is to determine, primarily, the characteristics of physiological materials impacted by a Voice-signal. Learning a Transfer path is a hunt for "hotspots," points (often considered Voice kernels) where either Voice-signal waves or physiological components in the system experience individual or collective energy loss or gain.

A central purpose of ML applications is to, ultimately, help decode the voice as a messenger, possessing explicit details of contours, functions and transformations within its "environment" (a physiology); data imperative to the invention's aim of Voice-driven internal imaging. It may be useful to clarify that the objective here is not to consider the voice as a "diagnostic" tool, wherein voice qualities (such as its frequency or signal-to-noise ratio) indicate a biomarker of physiological health (as in a voice-based diagnostic). Rather, the objective is to learn a voice as an encoded object possessing multifaceted, granular details about structural features within a domain. The incentive is, then, to extract and employ these granular details as image. In this case, a voice does not diagnostically point, like an arrow, to a prescribed value of wellness within a system. Rather, a decoded Voice-signal reveals an internal cartography, such as structural distances between organs, or patterns in tissue composition and becomes an independent utility for imaging.

To note, Voice-physiology Parameters and values can be obtained from Voice-signal data acquired before, during or after the act of voicing. Essential Voice-physiology measurements include Fundamental wave properties (frequency, wavelength, velocity, etc.).

Wave behaviors, like scattering, absorption, reflection, refraction and diffraction, are learned through Voice-signal Transfer path evaluations (and related Frequency response function analyses). Viscoelastic (material property) response to acoustic signal is assessed. Quantifying values of resonance, reverberation, shared systemic frequency excitement, and wave spread support learning the Voice-physiology terrain, its synchronicities and causalities. Body-based infrasonic waves (low-frequency vibrations produced by physiological processes), including heartbeats, respiratory movements, and blood flow in veins are measured, particularly, in relation to a Voice-signal. More examples of physiological values that can be measured are breath rate, breath speed, lung capacity, bodily fluid rates of flow, bodily fluid pressure, tissue density and temperature, distances between and dimensions of features of internal physiology and measurements of intrinsic system vibration.

"Call-and-response" dynamics are certainly prevalent within a Voice-physiology, such as the signal-response dynamics within patterns of upper-partial harmonics and their structural physiological impressions within the domain. The piezoelectric response within body structures can also be framed as a call-and-response dynamic. However, these state changes are not significant enough to validate an "impedance-based" approach for internal imaging utilizing Voice-driven means. Rather, a prime means of obtaining structural information from a Voice-signal comes from measuring changes in the arrival times of transmitted Voice-signals due to propagation velocities (ultimately, a focal aim of Transfer path analysis). In this case, transmission and arrival times are gauged through Voice-signals and a receiver (for example, a Signal-based instrument sensor), which help to provide information about the terrain, or the objects in the path between the source and receiver. In one method of collecting transmission and arrival times (data), a Rig (comprising at least two accelerometers) is applied to a front and back body in an aligned capacity, providing opportunity to measure signal and response from different points of the domain 207. This way, variations of arrival times can be determined, depending on the velocity changes within the interior of the body and the distinct locations of a Voice-signal.

Measuring the voice is like mining for gold. It includes determining where the greatest "mineral deposits" or valuable areas are located, and then developing the means to precisely extract that information in an (ideally) cost-efficient capacity. There is the arduous process of siphoning out, or extracting, essential "voice nuggets" from the "system noise" (careful to not undervalue, overlook or leave any stone unturned). And then, of course, comes the pristine care of polishing data.

CEC: A Phenomenological Digital Twin

Voice-physiology data is initially searched, learned and Optimized through ML methods involving a Phenomenological base-model; a first Digital twin 303. A Digital twin is a data-driven, digital representation of a biological asset (in this case, a Voice-physiology), built of statistics derived from its biological asset 301, 302, to which it is twinned. The Digital twin learns in both live and recorded situations, functioning in parallel operation with its biological twin (a Voice-physiology), obtaining training data in training experiments, saved as training examples. The obtained data supports its synthesis, and provides extensive material for learning and Meta-learning a domain.

A phenomenological Digital twin can learn empirically through training experiments, such as by "poking" a biological asset, wherein experiential learning environments are distinctly created for a Digital twin to gather data from its biological twin's elicited response. A "poking" condition can include obtaining simultaneous data from two different measuring instruments (for example, ultrasound and accelerometers) in one focused subregion of a Voice-physiology.

Another "poking" event can involve collecting data sets for comparing closed and open-mouthed voicings measured along various points of the Voice-physiology. Another "poking" instance, for example, is a training experiment involving an underwater Rig, recording signal propagation from front and back body points, wherein a Voice-physiology is underwater (aside from a Voicer's mouth that is not submerged). Signal-data propagation is then obtained terrestrially from the same front and back body points by a Rig to contrast with aquatically collected data. In this way, a digital twin gathers data in real-time, experienced along with a biological twin. In all "poking" instances, baseline factors related to breathing, body temperature, environment, etc. are considered. Creating well-controlled, "simplified," but diverse conditions for collecting broad sets of data provides a wealth of comparative learning opportunities within various training examples. The Phenomenological Digital twin can be trained with ML in both live or "offline" instances. ML helps to interpret the Digital twin, establishing initial Parameters relevant to features, essential relations, dynamic ranges and distances (Fundamental wave properties and Wave behaviors); which, in turn, support the foundation of developing a functional Voice-network 501.

Raw Data Development

While Base learning a Voice-physiology model is largely initialized in a supervised capacity, domain learning processes may also enlist multiple techniques within the ML family.

From early ML stages, learning is oriented towards graphically representing complicated structures in adaptive capacities, supporting thorough translation between developmental stages of the Pipeline. For example, where information about a Voice-physiology is obtained through various metrics (accelerometers read out in millivolts, frequency is described in Hz, pressure is gauged by Pascals, etc.), multiple SI units can be unified through computational metrics. Effective graphing methods are set up for Multi-scale modeling, wherein, for example, variations of electromagnetic, piezoelectric and metabolic elements (relative to Voice-signaling) are expressed in different time scales. Early-stage, Base learning processes are a hunt for patterns, functions and attributed features related to Voice-signal waves, enlisting, for example, Fourier and Wavelet transforms for analyzing the contributing components of harmonic structures. Early-stage ML is guided by general best approaches to learning Dynamic systems, creating groundwork for gaining initial insight into domain conditions. ML insights are Optimized and evolved (primarily through means of Evolutionary methods) with the intention to advance a Second-generation digital twin, implemented with Meta-learned statistical intelligence, a semi-empirical, Physics-informed hybrid model.

CEC: Optimizer

A Phenomenological digital model of the Voice-physiology undergoes a deeper design search through an Optimizer 304, a querying, strategizing and decision-making model. Querying can include EC methods of combining, building or sampling different data from various Neighborhoods of a domain, providing possible solutions ("candidate solutions") to determine the best elements relevant to a design strategy. Querying provides an input to a Digital twin, with a strategy to evolve probable solutions (searching relations, dynamics and conditions of the domain space). Decision-making processes determine what candidate solutions provide highest value (fitness), where a level of "fitness" is gauged by the best value of input as determined by the output (or response) of the twin. Evolutionary optimization methods within a Voice-network are similar to the methods of natural selection found in biology, wherein biological systems optimize operations (evolve) by selecting the most prime candidate solutions. Candidate solutions offer insights into a Voice-network, such as its causal relationships or organizational principles.

Querying processes, for example, evolve sets of differential measurements that inform system dynamics, such as learning (and Meta-learning) system changes during a "voiceless" exhalation and an exhalation that is "voiced." EC Meta-learns data, for instance, related to the propagation of a Voice-signal's change in velocity within the body's heterogeneous materials. Optimization methods Meta-learn Parameters for more efficiently factoring transmission times between a source and receiver. EC optimization also "fine-tunes" data relevant to Voice-signal impact on interstitial fluid states, obtained from multiple measuring instruments (for example, an endoscopic ultrasound, a Rig and diffused-weight MRI). Similarly, Optimization Meta-learns the impact of the voice on piezoelectric measurements of skin-signals. EC searches to approximate the contributing forces within a region of the Voice-physiology, as well as calibrations of whole-body vibration changes (explicit to voicing). In broadest terms, extending the library of discrete features of a voice and their signal significance within a physiology is an Optimization process, and stages of Optimization are key within the development of a CEC Pipeline for producing Voice-driven internal imaging.

To clarify, by design, a CEC pipeline 502 is Interoperable 305, 410 and, additionally, optimization can occur in all development stages. EC can optimize data structure, for example, such as a representation of Multi-dimensional data points relevant to signal information. To add, while methods of Optimization are often in the family of EC, system Optimization can also include varied approaches and applications, such as standard reinforcement strategies. EC, however, is also capable of Optimizing contributing applications or design approaches. For example, EC can Meta-learn insights provided by Topological data analysis (TDA), a math-driven means to explore data's topological and homotopic features (well-positioned for the Shape-based system-wide approach).

From the get-go, the design of the CEC Pipeline 502 is "bioinspired," primed to support learning and self-referential learning, to find usefulness, order, or function in chaos (as does a Dynamic system). Through Optimization methods, a digital model evolves to reveal correlations within the massive design space of a Voice-physiology, system-wide functions begin to crystallize, and what is "universal" about a Voice-physiology begins to take shape. Through strategies of Optimizing a Phenomenological Digital twin, it becomes possible to formulate essential mathematical principles about a Voice-physiology, which become the foundations of a next-stage hybrid model, a "Second-generation twin" 306.

CEC: A Hybrid Model, Second-Generation Digital Twin

A biological twin has been represented by its Digital twin, its data handled and sorted by ML. Base learning of the domain has been strategically Optimized. Referring to FIG. 4, now, through the implementation of math and physics a Second-generation digital twin is advanced 403. (To note, the use of "Second-generation digital twin" takes its name from methods of business-based digital modeling—but the name is well-suited, as this twin is an advancement from its first Phenomenological forebear).

A Second-generation digital twin 403 is a hybrid, semi-empirical model; it works synergistically with statistical input, and learns through interacting with the biological twin 401, 402. Yet, as a hybrid model, it is only semi-empirical, so, in some instances, its actions are justified by expressions in the form of mathematical equations, from having derived fundamental physical principles from statistics. A Second-generation digital twin is a Phenomenological model from first origin, so is still endowed with data-driven "DNA." However, it is capable of possessing high-value Multiphysics assets, ontological frameworks, and mathematically justified Rules of operation. Therefore, it is more focused, more effective, and more entrained to operate with the Voice-physiology as a useful, information-producing Voice-network.

A purpose for developing a Second-generation, Physics-informed, semi-empirical digital twin is to mathematically distill the principles of a Voice-physiology, so as to enable practical applications of a Voice-network. This stage of CEC development relies on a prudent approach, a delicate balance of simultaneously respecting the complex essence of a Dynamic Voice-physiology system while representing it in tractable means.

Within a Second-generation digital twin, formulas and equations derived from First principles are established through incorporating a priori information about Dynamic systems, estimation and validation processes, and through mathematical discernments. Second-generation digital twin data, including data specific to identified governing laws of the Voice-physiology, are learned, Optimized and adjusted through applied computational methods (including Evolutionary approaches.) In the hybrid model, a combination of "known physics" and "unknown" phenomena work together, the latter helping to develop the accuracy of the former, and the former making use of the latter for furthering operative applications. Reckoning underlying physical laws of the Voice-physiology supports the means to represent the domain mathematically through sets of system equations.

Multiphysics applications provide a deterministic method for evaluating different system physics simultaneously. For example, a Multiphysics application that is an Acoustic-structure interaction model provides insight into the causalities between a closed-mouth hum and emitted vibrational changes of a Thoracic spine.

Valuable from the onset of the CEC Pipeline, Multiscale modeling comes into special focus, specifically, during Second-generation digital twin developmental stages. Multiscale modeling provides a means to quantify system-wide mechanisms and gain useful insights into emergent patterns, such as large-scale phenomena arising from small-scale influences.

A Second-generation digital twin is supported by a judicious approach of evaluating the inherent structures of a Voice-network, and identifying the calculations and conditions of their transformations. Voice-network development also entails, in this case, a Shape-based Rule search using Topological data analysis (TDA), and EC Optimizes TDA search results.

The Second-generation digital twin learns from Finite element modeling (FEM), which facilitates concentrated means to solve differential equations. FEM supports defining Parameters and subdividing a Voice-network into elements to numerically solve functions such as wave interactions and structure dynamics, and EC methods Optimize insights offered by FEM.

Advancements in Second-generation digital twin development are inspired by Feature recognition methods, algorithmic approaches of augmenting data so a finer and fuller extent of physiological structures are reproducible through a Voice-signal. Augmentation methods borrow (in one example) from approaches in generative computer vision to relay a "fuller picture" about a Physiological configuration, generating new data through ML applications. Additionally, Second-generation digital twin development may enlist Reduced order modeling (ROM). ROM supports dimensionally reducing essential data about the Voice-network (including significant data pertinent to domain constitutions, functions, dynamic ranges, etc.), enabling a Voice-network to be represented as a compact model. Rather than sacrificing wide-spectrum domain operability, ROM positions a Voice-network to be more robustly effective in making accurate predictions, performing simulations and system-wide Optimization.

An apex of Second-generation digital twin development occurs when a learned input of a Voice-signal (biologically or digitally produced) is able to be outputted as a Configured internal physiology. This means that sufficient information has been extracted from a Voice-signal and its Transfer path to relay with accuracy the Geometries of a physiology, and an Optimized Voice-physiology is now a Voice-network, purposed and utilizable. Model development is now primed for final CEC operations, wherein a generated geometry 409 is a candidate Configured geometry of physiology and provided as input to a Simulator 404, and its simulation 405 is "checked" 406 and Optimized 407, for example, through EC methods.

CEC: Simulator

A Simulator 404 is built from the learned apex of Physics-based applications and methods deployed throughout Second-generation digital twin development, for example, Feature recognition methods, Generative learning approaches, Finite Element Modeling and Topological Data Analysis. A Simulator 404 is packed with processing ability to sum dynamic vibrational qualities (such as radiation patterns and source location) from values of Geometries of a Configured physiology; the product of a learned Voice-network. To maximize efficiency, a Simulator 404 can be built of Reduced-order modeling applications to extract and make use of the most essential Rules and transformations within a Voice-network.

The Simulator 404 is a configured, adaptable, functionally accurate model. It's given an input of a Configured physiology-a physiology that has been extracted and learned through the CEC Pipeline—from an original (digital or biological) Voice-signal source. From this input of a Configured physiology, a Simulator provides an output of a "matching" Voice-signal 405. A Simulator's accuracy of match is checked 406 by comparing the original correlated Voice-signal source with the outputted Voice-signal. Parameters and values of original Voice-signal data, correlated Configured geometries, and the outputted Voice-signal data are "fine-tuned" and Optimized. Optimizing a Simulator's matching function, in turn, Optimizes the accuracy of a Voice-network.

In one example of Optimization, candidate Geometries of physiologies are generated by evolutionary algorithms (EAs). EAs run "generations" of Configured geometries of physiology wherein the mark of fitness is the configuration that best matches the output of Voice-signal. The generations of geometries 409 closest to the Voice-signal get a high fitness value, which can then mean (in EA terms) a generated geometry has a "better chance of reproducing." In genetic (evolutionary) algorithms, "reproducing" is related to EA operators like recombination, mutation or cloning mechanisms.

End-to-end, EC methods support Optimization processes 304, 407 throughout the CEC Pipeline. In this instance, until the Simulator's Voice-signal output is a fit to its matching Physiological configuration, Evolutionary methods Optimize the Simulator for success, evolving gradient details and fineness of Resolution along the way. The effect, ultimately, is the solution to an Inverse problem, the final model operation.

Figure 5:
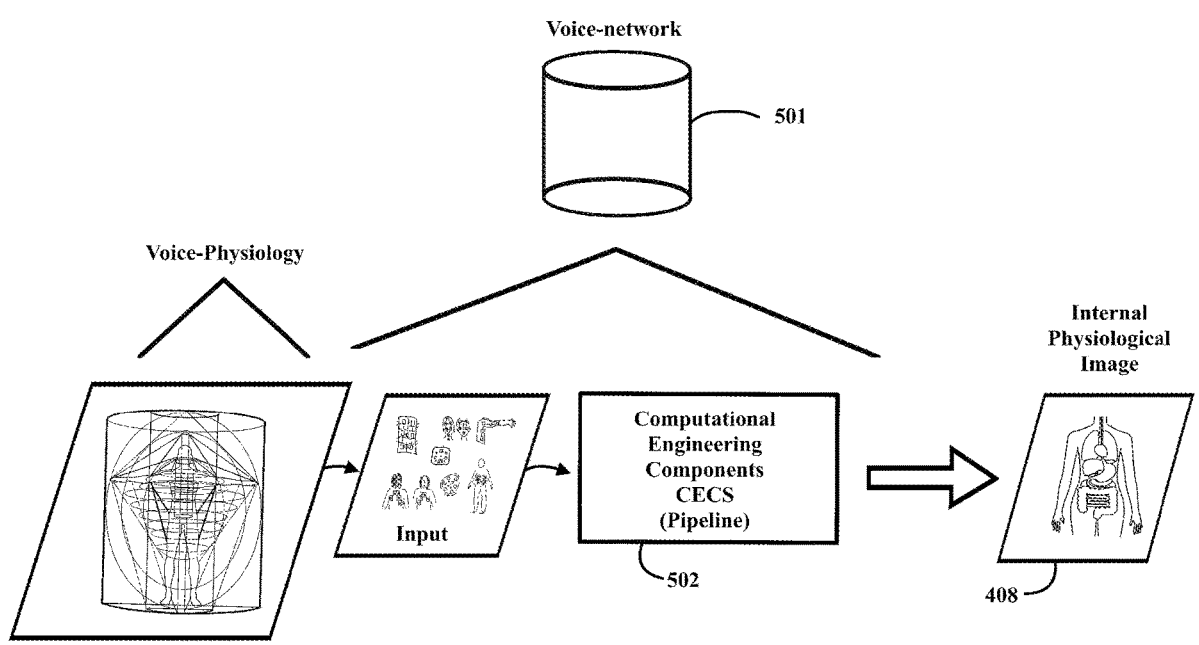
FIG. 5 illustrates the overarching method and system of the invention including the development of a Voice-network from learning a Voice-physiology.

Evolved to successfully output a high-level match of a Voice-signal from an inputted Configuration of physiology, conversely, a Simulator is programmed to output a physiology from the inputted Voice-signal data of one or more Voice-signals of a Voicer's voice. An output product of a Physiological configuration is an image data file 408 (shown in FIGS. 4 and 5) that can include (though is not limited to) features of tissue, bone, muscle, visceral organ, fluid and system dynamics. While the voice-image system and method herein described are primarily intended to be used with humans, they can also be applied to other living beings and animals, and even non-living objects, machines and other entities that produce and/or transmit vibrations.

As a rule, all singularly termed components can also indicate plural cases, and vice versa. Additionally, terminology including the use of "instrument" (relevant to collecting Voice-physiology data) refers to Signal-based measuring instruments. The use of term "Signal-based measuring instruments" may reference categories of both Non-imaging signal-capturing instruments and internal imaging-based instruments. To add: Depending on grammatical context or wording choice, usage of "Configured geometries of a physiology" can be substituted with terms "configured physiology," "configured geometries," "configured internal physiology," "geometries of a physiological configuration," "physiological configuration," and "geometries of physiologies" (as noted in glossary).

Glossary

ACOUSTIC-STRUCTURE INTERACTION: An equations-driven method to estimate the structural response of vibrational events. (See Multiphysics modeling.)

BASE LEARNING: Initial applications of machine learning statistical data of Phenomenological Digital twin, including supervised and other ML models.

CECs: (Computational Engineering Components) The digital machining and infrastructural system of modeling, Optimization and simulation that ultimately generates internal imaging, often interchangeable with what is considered the digital "Pipeline" of the computer architecture form and function. (See Pipeline.)

CONFIGURED GEOMETRIES OF A PHYSIOLOGY (configured physiology, configured geometries, configured internal physiology, physiological configuration): A term referring to any computationally (digitally) rendered region or subregion of a physiology that is a representation of a physiology, its form or function. A Configured geometry of a physiology comprises the geometries of any biological system of the body (i.e., endocrine, respiratory, digestive, circulatory or nervous system) and any elemental constituent of the physiology (hard and soft tissue, fluids, etc.) on macroscopic or microscopic levels.

CROSS-REFERENCING: Cross-referencing (or cross-training) data obtained by Signal-based measuring instruments. Cross-referencing can occur between Signal-based measuring instruments either of the same classification (for example, two Non-imaging signal-capturing instruments, such as an accelerometer and a pressure sensor), or between Non-imaging signal-capturing instruments (such as an accelerometer) and internal imaging instruments (such as ultrasound). Cross-referencing supports learning a Voice-network, correlating and comparing physiological features to Voice-signal data.

DIGITAL TWIN (Phenomenological model): A realistic digital representation of a Voice-physiology trained in live and off-line capacities, data-driven, and filled with statistics acquired by being "twinned" (connected directly) to its "biological twin" (a Voice-physiology) or receiving data from a Voice-physiology as an input. The Digital twin obtains "training data," learning empirically in "training experiments," saved as "training examples." The obtained data supports its synthesis, and provides extensive material for learning and Meta-learning a domain.

DYNAMIC SYSTEM: A Dynamic system framework supports learning (and meta-learning) a Voice-physiology as an inherent, organizational intelligence, offering a grounds-up approach for information acquisition and biomimetic design strategies, for decoding and deducing aspects of principles of "natural emergence" inherent within a Voice-physiology. Through a Dynamic systems perspective, a Voice-network is evolved as inter-operative, co-occurring, coevolving foundational "Rules" and "emergent" features, built from extrapolating essential, myriad-staged, multi-causal facets of a Dynamic Voice-physiology system. A Dynamic system exemplifies how small perturbations can deeply impact the overall state of a system, and supports investigating complex questions about the inter-relatedness of a whole system's parts. In this way, uncertainties can be framed as optimization problems, which is fundamental for the probabilistic modeling of the operative interactions between a Voice-signal and its Transfer path within a physiology.

EVOLUTIONARY COMPUTATION (EC, evolutionary approaches/methods): Referring to applications within the family of Evolutionary Computation (EC); methods motivated by the nature of biology for effectively addressing complex problems in areas such as computational design. EC, effectively, provides creative, search and exploration mechanisms for improving the performance, for example, of machine learning (ML) models. In the case of developing Voice-driven internal imaging, Evolutionary approaches can be used throughout the CEC Pipeline, for example, in feature selection (early data processing), resampling and Parameter setting (early ML and Meta-learning stages), evolving network topologies, in decision-making, Rule Optimization (in Optimization and Second-generation digital twin stages) and ensemble learning (Optimizing a Simulator).

FEATURE RECOGNITION: Feature recognition is the ability to automatically or interactively identify and learn shape information, Parametric information, geometric or topological properties of a region of interest; to assemble components and group features. It's an application, or means, for a model to detect, recognize, develop and improve distinguished features.

FINITE ELEMENT MODELING (FEM): A FEM is a general numerical method for subdividing a large system into smaller, simpler parts that are called finite elements, specific to the underlying physics of the system. Finite element models can predict the behavior of the system from given initial and boundary conditions measured at a few selected points.

FIRST PRINCIPLES: First principles are the identified foundational axioms supporting derived formulas and equations that can explain a system's governing laws (math and physics).

FITNESS FUNCTION: In Evolutionary Computation, a Fitness function is a design strategy that determines how "fit" or "good" a candidate solution is in respect to the considered objective.

FOURIER and WAVELET TRANSFORMS: A Fourier transform analyzes independent structures of a Voice-signal or physiological (mechanical) vibration, breaking down a whole signal into individual sinusoidal components of frequencies, extracted from a "time" domain. A Wavelet transform can describe signals both in time and frequency domain simultaneously.

FREQUENCY RESPONSE and FREQUENCY RESPONSE FUNCTIONS (FRF): FRF is a quantitative network analysis for evaluating system changes (magnitude, frequency, phase, non-linearity, resonance, damping) relevant to input and output differences. The Frequency response is a way to measure system stimulus, through quantifying an output of magnitude and phase in correlation to an input of frequency.

FUNDAMENTAL WAVE PROPERTIES (also "Voice-signal properties," as used in claims): Voice-physiology properties searched, learned and Optimized in the Voice-network and inherent to a Voice-signal, including essential core principles of mechanical waves, which are properties of frequency, amplitude, magnitude, periodicity, pressure, velocity, intensity and acceleration.

GENERATIVE LEARNING APPROACH (for data augmentation): Augmenting or increasing the quantity of data through algorithmically creating new data points from existing data.

GEOMETRIES of PHYSIOLOGY (geometries of a configured physiology, geometries of a physiological configuration): See Configured Geometries of a Physiology.

GEOPHONE: A measuring instrument, dominantly comprising a moving coil and magnets, using movement and suspension to induce a current which can then be used as an output proportional to velocity.

INTERFEROMETER: An Interferometer is an instrument that uses the constructive and deconstructive interference of acoustic or elastic waves to extract information about waves and the medium through which they propagate.

INTEROPERABLE: All stages of engineering design, including the CEC Pipeline and the method of assessing a Voice-Physiology are not limited to linear operation or development, but are able to make use of statistical insights and data advancements in agile and exchangeable means necessary for efficient production and processing of data.

META-LEARNING: Meta-learning (a subfield of artificial intelligence) is most commonly understood as learning to learn, which refers to the process of improving a learning algorithm over multiple learning episodes.

MULTI-DIMENSIONAL (data and analysis): Data representation of a Dynamic Voice-physiology system within formats representative of its varied dimensions; time-scales, reference frames, fidelities, functions and features (can be related to Multiscale modeling).

MULTIPHYSICS MODELING: A deterministic, mathematical model formulated as differential equations of (in this case) Voice-physiology kinetics. Multiphysics modeling offers tools for identifying mechanistic explanations of how complex biological behaviors arise. It can analyze interactions, for example, between structural mechanics and acoustic waves, piezoelectric effects, heat transfer, Acoustic-structure interaction, and pressure response and support the construction of well-represented, comprehensive and scalable graphs.

MULTISCALE MODELING: Multiscale modeling is implemented to identify causality and establish causal relations between data. To appropriately model a Voice-physiology, it is imperative to consider a Voice-signal in relationship to the stimuli within the domain, such as electromechanical activity, thermodynamic state changes and system flow-functions, and the different biological time scales of Voice-physiology components.

NEIGHBORHOOD: While this term is sometimes related to terms of "local regions," "subregions," "Spheres," "Slices," "sub-domains," "domains," it is, ultimately, attributed to points within a Voice-network. In topology, specifically, the term "Neighborhood" is used to describe points near a given point; it is a term that may be used to represent adjacencies within graphs. A Neighborhood of a point is a set of points containing that point where one can move some amount in any direction away from that point without leaving the set.

NODES: Nodes refer to "important" graphed points within dimensions of a Voice-physiology (or Voice-network) connected through relations (or edges) to other node points. There are often correlations between the terms Node and Voice kernel in describing the invention.

NON-IMAGING SIGNAL-CAPTURING INSTRUMENTS: Non-imaging signal-capturing instruments are, by design, technologies producing an output of signal-based data that is not a visual image of an internal form (whereas the term "visual image" denotes a technology such as a picture-based X-ray or MRI). Examples include accelerometers, pressure sensors, acoustic and/or elastic wave sensors (for example, Geophones or acoustic Interferometers), and piezoelectric probes.

NORMAL MODE: A Normal mode of an oscillating system is a pattern of motion in which all parts of the system move sinusoidally with the same frequency and with a fixed phase relation, activated by Voice-signaling.

OPTIMIZATION (Optimizer): A means and process of maximizing a model's performance. Optimization can be understood as an intelligent search and learning process, learning about the optimum, and, as an aspiration of exploration, efficiently sampling data with the goal of finding as "high of performing outcome as possible". Optimization can relate to an Optimizing model (Optimizer) or an Optimizing process.

PARAMETER: Parameters define characteristics of data, changing covariates or constants, as well as other values that can be reused during simulation. Model Parameters can relate to the statistics provided by the biological model, or learned from a digital twin or its simulations, estimated from data and required for making predictions.

PHENOMENOLOGICAL MODEL: See Digital Twin.

PHYSICS-BASED (or Physics-Informed): Means to translate a sophisticated system (such as a complex biological system) in computational terms of inputs to outputs, to provide a universal numerical, metrical mean to describe the functions and features of a Voice-physiology system. From this orientation, Physics-based operations can learn large data sets as foundational Rules, functorial transformations and higher category features, as constructed from the rewriting of base Rules, in applications including (but not limited to) Topological data analysis, Multiphysics modeling, Reduced-order modeling, Multiscale and Finite element modeling of the domain.

PHYSIOLOGICAL CONFIGURATION: See Configured Geometries of a Physiology.

PIPELINE: While most often referring to the Computational engineering components (CECs) of the invention, the term "Pipeline" encompasses the operation of (and Interoperability between) the system and method of the invention. The term "Pipeline" refers to all stages, features, and all algorithmic and engineering approaches executed to obtain, evaluate and adjust data towards clarifying the relationship between the voice and the physiology.

REDUCED-ORDER MODELING (ROM): Method of simplifying high-fidelity models while preserving essential behavior through complex mathematical algorithms. Particularly when united with capabilities of digital twins and ML, ROM can accelerate predictive computations. Through ROM, original data is projected onto a much smaller space, resulting in dimensionality reduction, aided by Principal Component Analysis (PCA), a system search to best represent data, revealing previously-unknown relationships, new data interpretations and enabling a greater capacity for simulation, Optimization and predictive computation.

RESOLUTION: Improving Resolution refers to "fine-tuning" a Voice-network through Optimizing metrics of Voice-signal properties and Wavie behaviors (such as velocity, measurements of wavelength, vibration. Frequency response and phase) for source reconstruction and gradient-based modeling applications. "Strengthening Resolution" of any data within any process or part of a CEC Pipeline is for the ultimate objective of producing an accurate and detailed match of a Configured physiology to a voice.

RIG: A Rig is a malleable, adjustable unit built for obtaining measurements of a Voice-physiology, comprising at least one accelerometer. The Rig is wearable as a "suit," "vest" or "patch," and is capable of being placed in precise arrangement on all parts of a Voice-physiology to obtain effective subsurface Voice-signal information about the area being measured. A Rig can be rotationally adjusted (clockwise and counterclockwise) to gauge, for instance, the time difference of arrival (transmission times) of a Voice-signal.

RULE: The core of a Voice-network can, in cases, be described as Rules for "rewriting" collections of relations, or Rules of repeated transformations and "patterns" (events, or "geometrizations"). A Rule specifies the calculation of an object that is intended to replace another object described by a pattern. Rules can also describe condition restrictions, relevant to strategies, combinations of order or limit of application, etc. The Rule-based programming style can support strategies to perform computations, or to perform deductions in situations where the inference Rules of logic are implemented as transformation Rules. (Also see Voice kernel.)

SECOND-GENERATION DIGITAL TWIN: A Second-generation digital twin provides the means to create more complicated relationships between Voice-physiology (and related Voice-network) structures, and facets and values within structures, allowing for a more connected data view of systems, foundations, structures and features of those structures. A hybrid-operating, Physics-informed, semi-empirical Second-generation twin is implemented with data (including statistical, learned, Meta-learned and Optimized) "intelligence" derived from a Phenomenological Digital twin. More equipped to recognize the features, processes, resources and essential Nodes, or Voice kernels of a Voice-physiology, a Second-generation digital twin's evolved structure results in advancing data insights.

SHAPE-BASED APPROACH: A Shape-based approach is substantial to Voice-Driven Internal Physiology frameworks and applications; including processes of demarcating a Voice-physiology in Spheres and Slices, capturing, learning, Meta-learning and Optimizing voice-signal data, and the Pipeline development of a Voice-Network. Decoding underlying Rules, mathematical transformations and emergent structures of a Voice-network is supported by a Shape-based approach. A Shape-based approach is a bridge, helping to synergistically position the natural geometries and organizational principles of a Dynamic system as a guiding influence in the development of a digital representation.

SIGNAL-BASED MEASURING INSTRUMENTS: Instruments comprising two categories of Voice-physiology measurement approaches: "Non-imaging signal-capturing instruments" (accelerometers, pressure sensors, etc.) and "internal imaging technologies" (i.e., ultrasound, MRI, X-ray, etc.).

SIMULATOR: A configured, adaptable, functionally accurate model with efficient compute resources, capable of accessing various processes for replicating (or extracting), learning or Meta-learning voice-signal data and correlated physiological geometries.

SPHERES and SLICES: A Voice-physiology that is considered in sectionalized assemblies. "Spheres" dominantly describe geometries such as a cylindricality of a Voice-physiology area, while "Slices" can describe lines, connected points, or various intersections within a Voice-physiology. Spheres and Slices can encapsulate highly resonant intersections, vibrationally correlating structures, or distinct spatial distances, and support a Shape-based approach of obtaining useful metrics of the voice (data).

SYSTEMIC VOICE ENERGY: A comprehensive sum of all surmisable wave properties and Wave behaviors within a Voice-physiology from a Dynamic system perspective, considering a Voice-signal in relation to voicing and Voice-signal interaction in relation to the plethora of operating signal-based systems within a Voice-physiology.

TOPOLOGICAL DATA ANALYSIS: A field of computational mathematics for studying the shape of data at multiple scales, often supported by tools of persistent homology (PH). Homology refers to the characterization of topological features in a dataset, and persistence describes the extent to which these features persist within the data as a scale Parameter varies. TDA (with PH) can be useful for analyzing networks, data sets and graphs, and for extracting accurate estimates of Parameters from models of inherently noisy systems, like Dynamic Voice-physiology systems. TDA can help give more information to outputs than just "predicted" numbers, but information about relational qualities within data.

TRANSFER PATH: The Transfer path relates to a Voice-physiology's internal vibrational, signal-response chain, and can be represented graphically through Nodes of structures and edges of Voice-signal transmissions. The Transfer path notes Voice-signal qualities and behaviors such as frequency, range, propagation, pressures, oscillations, vibration, harmonics; and Voice-signal instigated emergent, intersective and dynamical expressions.

TRANSFER PATH ANALYSIS (TPA): is a technique used to break down a Voice-signal into its key contributors, wherein points along a Transfer path represent a database of stored information about signal transfer pathways that can provide information about dynamic Voice-physiology interplay. TPA helps to distinguish key interactive Voice-physiology points, particularly in "hotspots" where the Voice-signal and/or physiological components experience energy loss or gain, absorption or transmission.

VOICE-DRIVEN: In this disclosure, Voice-driven does not mean, as it may in other fields of engineering, "powered by" (as in made active) by an energy source such as solar or nuclear power, for example. Rather, "Voice-driven," in the case of Voice-driven internal imaging, denotes making use of a voice as a complete, signal-encoded system unto itself; inputting and decoding Voice-signal data to solve for unknown dynamic components between the voice and the physiology. Thus "Voice-driven" internal imaging inputs Voice-signal data to produce the output of an internal image (an image data file).

VOICE KERNEL: A Voice-physiology (and Voice-network) can be learned as emerging from a system of Voice-signal Rules that generate combinations of executions, operations or transformations, in relation to a physiology; a causal network of signal responses.

Voice kernels are important points, Nodes, or Rules that help define the "cartography" of a Voice-physiology, exemplifying an underlying set of transformational Rules, from which geometries, features, dynamics, etc. emerge. These points can be identified both as primary implications of voicing as well as (and especially) where structural response and Voice-signals effect new causal paths within a system. (Also see Rule and Node.)

VOICE-NETWORK: The use of the term Voice-network most often refers to the process of digitally learning and operating a synthesis/model of a Voice-physiology domain. A Voice-network is often presented in Multi-dimensional graph-form, expressing the formulaic foundations, transformations and emergent geometrized features of a user's voice (Voicer) in their own body system and the causal relation between the voice and the physiological infrastructure of the body. A Voice-network enables Voice-signals and the learned Voice-physiology to work as agents of the invention. The Voice-network is the constructed, motile, map of the Voice-physiology as a Dynamic system, a learned, applicative digital translation of a biological model of Voice-physiology. A Voice-network employs a Voice-physiology as a canvas for applied math and physics.

VOICE-PHYSIOLOGY: A Voice-physiology is a complete domain that is a Dynamic system and composed of states and state shifts within a physiology relevant to before, during or after the signaling of a voice. The Voice-physiology provides a causal network of signals capable of exhibiting nonlinearities and involving different variables (for example signals of Fundamental wave properties and Wave behaviors and their effects on system functions and system compositions). In relation to the CEC Pipeline (and, specifically, digital twin processes) terms "biological asset." "biological model," or "biological twin" refer to the Voice-physiology.

Furthermore, Voice-physiology is broken down into each term within its compound (voice and physiology), to give parts specification to the partnered combination, and then re-summarized, again, after specified in parts:

a. The Voice: In all instances relevant to this disclosure, a voice is not associated with the "symbolic architectures" of language, "meaning-making," or utterances executed towards the emergence of lingual formation (such as parts of lexical speech, mimicries, etc.). Rather, the voice is regarded as a force-a vibrational, propagational energy—acting within a medium, produced by a Voicer. Voice behaviors, additionally, apply solely to the voice's implication within its own physiology (rather than an externalization of voice, projected outwardly, or impacting another, or relevant to any/all psycho-emotional aspects of communication). The voice is considered as an encoded object possessing multifaceted, granular details about structural features within a domain, and the incentive of the invention is, then, to extract and employ these granular details as image.

b. The Physiology: A region demarcated as the perimeter of geometries relevant to the area of the body, including distinct geometries of space directly around the body as well as the physical form and its physiological attributes.

c. Voice-physiology: The Voice-physiology demarcates a human physiology as a domain that is a "containing system" for all Voice-signals, wherein the implications of a voice within a Voice-physiology are considered as a Dynamic system. A Voice-physiology includes all directly and indirectly interconnected Voice-driven, Voice-signal and response patterns considered within a whole physiology. A Voice-physiology is not constricted by, nor limited to "local" anatomies most-often associated with speech and lexically-oriented sound (larynx, pharynx, tongue, etc.), but considers the complete physiology and body, including vibrationally-transmitting regions like the navel, cervical vertebrae, bottoms-of-feet, interstitial fluids, the spine, and is considered through its geometries, such as symmetries and ratios.

VOICER: One who produces voice through the operative means of their own physiology. In Voice-driven internal physiological imaging, a Voicer's Voice-signal input allows for the output, that is, the imaging of their internal physiology.

VOICE-SIGNAL: Referring to the implications of a Voicer's voice, and all voice-instigated vibrations and oscillations within a Voicer's own physiology. In the case of the invention, Voice-signal is used rather than "sound-signal," as a voice is not considered in realms of its sound ("heard," mechanical waves), but more-so in a vibrational context. "Voice-signal" is useful in the instance of describing accelerometer-based measurements, as an accelerometer, to note, does not measure "sound," but does gauge vibration.

In whole, an expressed Voice-signal is not a singly operative "sinusoidal" wave (though can be analyzed by its sinusoidal parts). A Voice-signal, rather, is a composite of signals emitted from one or more voice instigated vibrational sources within a physiology. The "composite" can be described as a collection of "nonlinearly coupled oscillators" in a "Multi-dimensional array."

WAVE BEHAVIORS (or Waving behaviors): Qualities most relevant to the (complex) waving behaviors within a Dynamic Voice-physiology system, beginning with propagational behaviors of scattering, absorption, reflection, refraction, diffraction and impedance. Within a Voice-physiology, Wave behaviors can include intrinsic ambient and background "noise," pressure variations, vibrational directivity, wave displacement, damping, frictional or dissipative forces, penetration, attenuation, wave spread patterns, linear and non-linear behaviors, reverberation, viscoelastic response to acoustic signal, resonance, shared systemic frequency excitement (natural and preferred frequencies), interactive Dynamic system response signals (such as coupling oscillations), harmonic structures and harmonic vibration (periodic vibration where the values of the vibration Parameters can be described as sinusoidal functions of the independent time variable), resonance, interference, phase and phase-locking, system-wide synchronic and causal implications, force, "whole-body vibration" (mechanical vibration transferred to the body), and vocal interaction with biological vibrations (for example, infrasonic waves generated by physiological processes-such as heartbeats, respiratory movements and blood flow in vessels).

I claim:

1. A method of converting captured voice-signals of a voicer's voice into true images of said voicer's body and of features of said voicer's internal physiology, comprising the steps of:

selecting a voicer capable of producing a voice-signal and having a body with an internal physiology, wherein a voice-signal comprises vibrational principles and waving behaviors, and implications of the vibrational principles and waving behaviors instigated by said voicer's own voice on said voicer's own body and internal physiology; demarcating a region of said voicer's body;

collecting physiological values from said voicer, said physiological values comprising one or more of breath rate, breath speed, lung capacity, bodily fluid rates of flow, bodily fluid pressure, tissue density and temperature, measurements of intrinsic system vibrations and distances between and dimensions of features of internal physiology;

building a first phenomenological digital twin using data comprising said physiological values;

configuring one or more signal-based instruments, selected from a first group comprising non-imaging signal-capturing instruments and internal imaging instruments, to capture one or more of voice-signal data and physiological values from said region;

capturing one or more of voice-signal data or physiological values from said voicer at one or more times selected from a second group of before, during and after voicing, using said one or more signal-based instruments;

training a first phenomenological digital twin with said one or more of voice-signal data and physiological values;

learning and identifying one or more voice-signal properties and waving behaviors from said first phenomenological digital twin using one or more machine learning methods, wherein said voice-signal properties and waving behaviors comprise one or more of: velocity, wavelength, frequency, vibrational directivity, wave spread, pressure variations, multivariate wave interactions, points along wave transfer paths, absorption, reflection, refraction, diffraction, and scattering wave behaviors, resonance, reverberation, and shared systemic frequency excitement;

optimizing said captured voice-signal data and said learned voice-signal properties and waving behaviors within said first digital twin using one or more machine learning methods, said one or more machine learning methods comprising at least an evolutionary computation method, thereby evolving a voice-network, which has parameters and values which digitally represent voice-signal properties and waving behaviors correlated to features of internal physiology, wherein each said feature has at least one geometry;

building a second-generation semi-empirical digital twin by inputting data from said first digital twin and enabling one or more applications comprising multiphysics modeling, multi-scale modeling, topological data analysis, finite element modeling, and reduced order modeling;

training said second-generation digital twin with additional captured voice-signal data and physiological values from said voicer;

learning, meta-learning and optimizing said second-generation digital twin data using one or more machine learning methods comprising at least an evolutionary computation method, thereby continuing to evolve said voice-network in order to more closely correlate said geometries of internal physiology with voice-signal data;

generating one or more candidates of said geometries of internal physiology from source voice-signal data using machine learning methods;

building a simulator from said parameters and values of said voice-network using physics-informed modeling processes, comprising one or more of finite element modeling and reduced-order modeling;

inputting said one or more candidates into said simulator, wherein said simulator converts said inputted candidates to outputs of voice-signal data, which are attempts at matches;

checking each said outputted voice-signal data against its source voice-signal data, and comparing the original correlated source voice-signal data with the outputted voice-signal data, thus confirming the accuracy of match between each said outputted voice-signal data and its correlated candidate;

optimizing generations of said candidates using methods of machine learning through repeating said generating, inputting and checking steps, and establishing a fitness value, wherein higher fitness values are assigned to those generations of said candidates closest to the simulator's voice-signal data output;

repeating said optimization of generations of candidates step with a goal of improving said fitness value, thereby optimizing the accuracy of match; and inputting a voice-signal into said simulator, and receiving an output of a true image of features of internal physiology, comprising an image data file.

2. The method of claim 1, wherein said demarcated region comprises said voicer's whole body.

3. The method of claim 1, wherein a shape-based approach is used in one or more demarcating, collecting, configuring and capturing steps, wherein said body has inherent mathematical symmetries, ratios and geometries consistent with understanding said body and said features of internal physiology as a structure for vibrational interactions, and wherein said shape-based approach comprises identifying and using one or more mathematical principles, symmetries, ratios and geometries of said body.

4. The method of claim 3, wherein said body has a navel and a spine, and wherein said demarcated region includes voicer's navel and spine.

5. The method of claim 1, wherein a shape-based approach is used in one or more building, learning, training, identifying, optimizing, generating and checking steps, wherein said shape-based approach comprises identifying underlying mathematical rules and emergent geometries of said voice-network using at least one of multiscale modeling, topological data analysis, and graphical representation of nodes and transformations of said voice-network.

6. The method of claim 1, wherein one or more of said training, learning, optimizing and checking steps further comprises cross-referencing a first member of a third group with a second member of said third group, said third group comprising voice-signal data captured with said non-imaging signal capturing instruments; physiological values captured with said non-imaging signal-capturing instruments; voice-signal data captured with said internal imaging instruments; and physiological values captured with said internal imaging instruments.

7. The method of claim 1, wherein one or more of said learning, optimizing and generating steps further comprises one or more of employing a generative learning approach and a feature recognition method which augments data.

8. The method of claim 1, wherein said configuring and capturing steps further comprise one or more measuring approaches selected from a group comprising capturing transmission and arrival times of a voice-signal, and obtaining voice-signal data and physiological values along a voice-signal's transfer path.

9. The method of claim 1, wherein said configuring step further comprises using one or more arrays of two or more signal-based instruments chosen from a fourth group comprising accelerometers, pressure sensors, acoustic wave sensors, elastic wave sensors and piezoelectric probes, and said arrays being configured to each rest on a surface of said body, and to rotate on said surface.

10. The method of claim 9, wherein said one or more arrays comprises a plurality of arrays, and wherein each said array has an axis of rotation which extends perpendicular to said array through said body, and wherein two said arrays rest on opposite surfaces of said body, and share an axis of rotation.

11. The method of claim 9, wherein said fourth group further comprises ultrasonic imaging instruments.

12. The method of claim 1, wherein said voicer is a non-human living entity.

13. The method of claim 1, wherein said voicer is a vibration-transmitting non-living entity, comprising an object or a machine; and wherein said voicer's body and internal features comprise the physical structure and internal functions of said voicer.

14. A system for converting captured voice-signals of a voicer's voice into true images of said voicer's body and features of internal physiology, comprising:

one or more signal-based instruments, selected from a first group comprising non-imaging signal-capturing instruments and internal imaging instruments, each signal-based instrument being configured to capture one or more of voice-signal data, physiological values and internal images from a selected region of said voicer's body; and a memory that stores data and computer executable components; and one or more processors that execute said computer executable components stored in said memory, wherein said computer executable components comprise:

a training component that employs one or more machine learning methods to train a digital twin with at least one of said voice-signal data and physiological values;

a learning component that employs one or more machine learning methods, comprising at least an evolutionary computation method, to learn, meta-learn and optimize voice-signal data and physiological values;

a generating component that creates configurations of features of internal physiology from source voice-signal data;

a simulation component that outputs voice-signal data from inputted configurations of features of internal physiology, and that outputs an image data file from an inputted voice-signal; and a checking component that assesses accuracy of match between voice-signal data outputted by said simulation component and source voice-signal data which was used by said generating component to create a correlating said configuration of features of internal physiology.

15. The system of claim 14, further comprising one or more means for obtaining reference images of said voicer's body via at least one of an ultrasound scanning technique, magnetic resonance imaging (MRI), acoustic tomography, echocardiogram and magnetoencephalography (MEG).

* * * * *